(12) United States Patent
Liversidge et al.

(10) Patent No.: US 6,432,381 B2
(45) Date of Patent: *Aug. 13, 2002

(54) METHODS FOR TARGETING DRUG DELIVERY TO THE UPPER AND/OR LOWER GASTROINTESTINAL TRACT

(75) Inventors: Gary G. Liversidge, West Chester; W. Mark Eickhoff, Lansdale; Kathleen J. Illig, Phoenixville; Pramod Sarpotdar, Malvern; Stephen B. Ruddy, Schwenksville, all of PA (US)

(73) Assignee: Elan Pharma International Limited, Shannon (IR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/815,346

(22) Filed: Mar. 11, 1997

Related U.S. Application Data

(63) Continuation-in-part of application No. 08/366,841, filed on Dec. 30, 1994, now Pat. No. 5,628,981.

(51) Int. Cl.$^7$ .......................... A61K 49/00; A61K 9/14; A61K 9/50
(52) U.S. Cl. ...................... 424/1.29; 424/489; 424/495; 424/499; 424/501; 424/9.4
(58) Field of Search .............................. 424/1.29, 489, 424/495, 499, 501, 9.4; 514/951

(56) References Cited

U.S. PATENT DOCUMENTS 5,145,684 A * 9/1992 Liversidge et al. ......... 424/489
5,326,552 A * 7/1994 Na et al. ..................... 424/9.4

* cited by examiner

Primary Examiner—Michael G. Hartley
(74) Attorney, Agent, or Firm—Foley & Lardner

(57) ABSTRACT

Particulate crystalline therapeutic substances are formulated with stabilizers to enhance contact between the crystalline therapeutic substances and the mucosal membranes to provide extended therapeutic effect.

27 Claims, No Drawings

METHODS FOR TARGETING DRUG DELIVERY TO THE UPPER AND/OR LOWER GASTROINTESTINAL TRACT

RELATIONSHIP TO OTHER APPLICATIONS

This is a continuation-in-part of application Ser. No. 08/366,841, filed Dec. 30, 1994, U.S. Pat. No. 5,628,981.

BACKGROUND OF THE INVENTION

1. Field of the Invention

This invention relates to improved formulations of poorly soluble crystalline therapeutic agents which are absorbed through mucous membranes.

2. Background of the Invention

There is a constant need in the pharmaceutical industry for improved pharmaceutical formations which enhance the efficacy of poorly soluble therapeutic agents. There is especially a need for formulations that (1) enhance the adsorption of poorly soluble therapeutic agents across mucous membranes or (2) extend the period of time that poorly soluble therapeutic agents useful for treating of a site have contact with the mucosa of the site.

Since most poorly soluble crystalline therapeutic agents do not inherently adhere to mucosal surfaces, there is a need to provide in such formulations, primary surface active stabilizers with appropriate mucoadhesive properties and secondary excipients that provide for an improvement in therapeutic efficacy as compared with existing products and formulations. Therefore, the physical-chemical properties of the therapeutic agents, and any desired surface active stabilizers and viscosity modifiers must be taken into consideration.

The identification of surface active stabilizers for use with small particles of crystaline poorly soluble drugs, wherein the surface active stabilizer has bioadhesive or mucoadhesive properties to mucous membranes, in particular, to the entire GI tract, has not been reported to date. The development of appropriate surface active stabilizers that will enable mucous membranes to be utilized to enhance bioavailability represents a difficult technical problem.

Bioadhesion is usually achieved by interaction of either a synthetic or natural polymeric substance with mucosal membranes. Such technology has been employed to enhance drug delivery by decreasing the transit time of a drug substance in the GI tract and hence promote an opportunity for enhanced absorption. Highly charged carboxylated polyanions are good candidates for use as bioadhesives in the GI tract. See, for example: Park, K. and Robinson, J. R., Bioadhesion: Polymers and Platforms for Oral-Controlled Drug Delivery; Method to Study Bioadhesion. Int. J. Pharm., 19, 107 (1984). The formation of a bioadhesive bond between a polymeric substance and the mucosal lining of the GI tract can be visualized as a two step process, i.e., initial contact between the two surfaces and the formation of secondary bonds due to non-covalent interactions. Bioadhesives specific for mucous membranes must interact with the mucus layer during attachment. Mucus, a general term for the heterogenous secretion found on the epithelial or endothelial surfaces of the mucous membranea, is made of the following components: glycoprotein macromolecules, inorganic salts, proteins, lipids and mucopolysaccharides. These glycoproteins typically consist of a protein core with carbohydrate side chains. This forms a network of mucus that is a continuous layer covering the muscous membrane. From a bioadhesive perspective, mucus consists of highly hydrated, crosslinked linear, flexible yet random coiled glycoprotein molecules with a net negative charge. Understanding the principles of bioadhesion is the basis for producing an improved formulation for poorly soluble therapeutic agent. Bioadhesion accounts for the interaction between a biological surface and a biomaterial substance. As noted previously, bioadhesive agents are usually polymeric substances that adhere to tissues by ionic or covalent bonds or by physical attachment. Several theories of bioadhesion have been published including electronic, adsorption, wetting, diffusion and fracture theories. Bioadhesives bind to membrane surfaces and are retained for variable periods of time.

The primary difficulty with previously reported mucoadhesive stabilizers is that they do not interact effectively with both the particles of the therapeutic agent and mucous membrane uniformly so that, e.g., both the upper and lower GI tract can be used as sites to increase bioavailability. The stabilizers used for this purpose must be adsorb sufficiently to the different regions of the GI tract. In practice, stabilizers tend to be adsorbed at some biological surfaces differentially than at others due to a variety of complex reasons. There is a need for formulations of particles of therapeutic agents that are adsorbed sufficiently over the entire mucous membrane.

It has now been discovered that particles of crystalline therapeutic agents modified by having a poloxamer absorbed on the surface thereof, can be adsorbed onto the mucosal surface, including the GI tract.

In another embodiment the present invention relates to improved formulations of therapeutic agents, including gastrointestinal therapeutic agents, wherein the formulations provide prolonged local contact of the therapeutic agents with the mucosal layer, including the gastrointestinal tract.

SUMMARY OF THE INVENTION

In accordance with the present invention, there is provided a therapeutic composition comprising:

from about 0.1% to about 45% w/v, and, preferably, from about 0.5% to about 15% w/v, of particles of a poorly water-soluble crystalline therapeutic agent having a weight average particle size of less than about 2,000 nm, more preferably, a weight average particle size of less than about 1,000 nm, and most preferably, a weight average particle size of less than about 400 nm;

from about 0.1% to about 10% w/v, and preferably of from about 0.25% to about 5% w/v of a poloxamer; and water to make 100% w/v.

These compositions can be administered by any route that will result in the therapeeutic agent having contact with a mucous membrane. These routes include oral, rectal, nasal, occular, inhalation and vaginal. Preferred is oral and rectal because the compositions of the present invention will enable the thereapeutic agent to be adsorded across the mucous mebrane of the entire GI tract resulting in greatly enhance adsorption.

Secondary stabilizers may also be used in the therapeutic composition up to about 1% w/v, preferably up to about 0.2% w/v, and most preferably up to about 0.1% w/v. Secondary stabilizers include dioctylsulfosuccinate (DOSS) and sodium lauryl sulfate (SLS).

Other ingredients customarily used in pharmaceutical formulations may also be included, such as flavorants, colorants and preservatives to provide pharmaceutically acceptable and palatable formulations.

The poloxamers useful in the present invention have an average molecular weight of from about 1,000 to 15,000 daltons; preferred have an average molecular weight of about 5,000 to 15,000 daltons.

Poloxamers are polyethylene-polypropylene glycol block polymers containing ethylene oxide (PEO) and propylene oxide (PPO) moles according to the formula $$(PEO)_a-(PPO)_b-(PEO)_c.$$

Preferred are poloxamers wherein;

a is 46 to 128;

b is 16 to 67; and c is 46 to 128.

More preferred are poloxamers wherein;

a is 46, 52, 62, 75, 97, 98, 122 and 128;

b is 16, 30, 35, 39, 47, 54 and 67; and c is 46, 52, 62, 75, 97, 98, 122 and 128.

Table 1 shows the various poloxamers by manufacturer-designated number.

TABLE 1

Molecular Weights of Poloxamers

| Poloxamer No. | Pluronic | Av. Mol. Wt | Av. Values a | b | c |
|---|---|---|---|---|---|
| 401 |  | 4,400 | 6 | 67 | 6 |
| 402 |  | 5,000 | 13 | 67 | 13 |
| 403 |  | 5,750 | 21 | 67 | 21 |
| 407 | F127 | 12,000 | 98 | 67 | 98 |
| 331 |  | 3,800 | 7 | 54 | 7 |
| 333 |  | 4,950 | 20 | 54 | 20 |
| 334 |  | 5,850 | 31 | 54 | 31 |
| 335 |  | 6,000 | 38 | 54 | 38 |
| 338 | F108 | 15,000 | 128 | 54 | 128 |
| 282 |  | 3,650 | 10 | 47 | 10 |
| 284 |  | 4,600 | 21 | 47 | 21 |
| 288 | F98 | 13,500 | 122 | 47 | 122 |
| 231 |  | 2,750 | 6 | 39 | 6 |
| 234 |  | 4,200 | 22 | 39 | 22 |
| 235 |  | 4,600 | 27 | 39 | 27 |
| 237 | F87 | 7,700 | 62 | 39 | 62 |
| 238 | F88 | 10,800 | 97 | 39 | 97 |
| 212 |  | 2,750 | 8 | 35 | 8 |
| 215 |  | 4,150 | 24 | 35 | 24 |
| 217 | F77 | 6,600 | 52 | 35 | 52 |
| 181 |  | 2,000 | 3 | 30 | 3 |
| 182 |  | 2,500 | 8 | 30 | 8 |
| 183 |  | 2,650 | 10 | 30 | 10 |
| 184 |  | 2,900 | 13 | 30 | 13 |
| 185 |  | 3,400 | 19 | 30 | 19 |
| 188 | F68 | 8,350 | 75 | 30 | 75 |
| 122 |  | 1,630 | 5 | 21 | 5 |
| 123 |  | 1,850 | 7 | 21 | 7 |
| 124 |  | 2,200 | 11 | 21 | 11 |
| 101 |  | 1,100 | 2 | 16 | 2 |
| 105 |  | 1,900 | 11 | 16 | 11 |
| 108 | F38 | 5,000 | 46 | 16 | 46 |

Certain number of these poloxamers are also known as Pluronic, which is a brand name of BASF Corporation.

Preferred poloxamers for use in the present invention are:

Pluronic F127

Pluronic F108

Pluronic F98

Pluronic F87

Pluronic F88

Pluronic F77

Pluronic F68 and

Pluronic F38.

DETAILED DESCRIPTION OF THE INVENTION

The present invention is based on the discovery that particulate crystalline materials can be rendered mucoadhesive or bioadhesive, especially in the gastrointestinal tract, when the particles of poorly soluble crystalline therapeutic agents have certain poloxamers adsorbed on their surface.

The invention can be practiced with a wide variety of crystalline agents that are water-insoluble or poorly soluble in water. As used herein "poorly soluble" means that the agent has a solubility in aqueous medium of less than about 10 mg/ml, and preferably of less than about 1 mg/ml, must preferably less than 0.1 mg/ml. Examples of preferred crystalline agents follow.

Therapeutic Agents

Suitable therapeutic agents can be selected from a variety of known classes of drugs which are known to be absorbed across muscous membranes, including, for example, analgesics, anti-inflammatory agents, anthelmintics, anti-arrhythmic agents, antibiotics (including penicillins), anticoagulants, antidepressants, antidiabetic agents, antiepileptics, antifungal agents, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, protease inhibitors, prostaglandins, radio-pharmaceuticals, sex hormones (including steroids), anti-allergic agents, stimulants and anoretics, sympathomimetics, thyroid agents, vasodilators and xanthines.

Especially preferred are those drugs that are absorbed in the GI tract, such drugs, include, for example, antacids, anti-inflammatory agents, antibiotics (including penicillins), antimycobacterial agents, antiviral agents, corticosteroids, parasympathomimetics, radio-pharmaceuticals, sympathomimetics, demulcents, emollients, gastrointestinal protectives and adsorbents, antifungals, H2-blocking agents, proton pump inhibitors, muscarinic antagonists, bismuth compounds, sucralfate, carbenoxolone, prostaglandins, digestants, bile acids, laxatives, antiparasitic agents, anthelmintics, antiprotozoal agents, antimicrobial agents, vitamins, immunologic agents, vaccines, anesthetics, lipid-regulating agents and bile acid sequestrants.

A description of these classes of drugs and a listing of species within each class can be found in Martindale, The Extra Pharmacopoeia, Twenty-Ninth Edition, The Pharmaceutical Press, London, 1989, the disclosure of which is hereby incorporated by reference in its entirety. The drug substances are commercially available and/or can be prepared by techniques known in the art.

Preferred therapeutic agents include those intended for oral administration and rectal administration.

Method of Preparing the Particles of the Therapeutics Agents

As used herein, particle size is determined on the basis of weight average particle size as measured by conventional particle size measuring techniques well known to those skilled in the art, such as sedimentation field flow fractionation, photon correlation spectroscopy, or disk centrifugation. In present invention, the weight average particle size of the crystals of therapeutic agent and surface modifier is less than about 2,000 nm, preferred is less than about 1,000 nm, and more preferred is less than about 400 nm. It is particularly preferred that the particles of the present invention have an effective particle size which is less than 2,000 nm, the preferred 1,000 nm or the more preferred 400 nm. By "effective particle size" is meant that at least 90% of the particles in the sample measured by the above-noted weight sizing techniques have a particle size less than the stated size. With reference to the effective particle size, it is more preferred that at least 95% and, even more preferably, at least 99% of the particles have a particle size less than the desired particle size.

The particles of this invention can be prepared in a method comprising the steps of dispersing a therapeutic agent in a liquid dispersion medium and applying mechanical means in the presence of grinding media to reduce the particle size of the therapeutic agent to the desired effective average particle size. The particles are reduced in size in the presence of the poloxamer. Alternatively, the particles can be intimately mixed with a poloxamer after attrition.

A general procedure for preparing the particles of this invention is set forth below. The therapeutic agent is obtained commercially and/or prepared by techniques known in the art in a conventional coarse form. It is preferred, but not essential, that the particle size of the coarse substance selected be less than about 100 microns as determined by sieve analysis. If the coarse particle size of the substance is greater than about 100 microns, then it is preferred that the particles of the substance be reduced in size to less than 100 microns using a conventional milling method such as airjet or fragmentation milling.

The mechanical means applied to reduce the particle size of the substance conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. We have found that zirconium oxide, such as 95% ZrO stabilized with magnesia, zirconium silicate and glass grinding media provide particles having levels of contamination which are believed to be acceptable for the preparation of pharmaceutical compositions. However, other media, such as stainless steel, titania, alumina, and 95% ZrO stabilized with yttrium, are expected to be useful. Preferred media have a density greater than about 3 $g/cm^3$.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the therapeutic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 $kg/cm^2$) are typical of media milling.

The particle size was determined during the milling process and again immediately before the suspensions were administered. Particle size was determined on the Coulter Model N4MD Submicron Particle Analyzer (Coulter Corp.; Miami Lakes, Fla.); and using the Microtrac Ultrafine Particle Analyzer (Leeds and Northrup Co.; St. Petersburg, Fla.).

The following formulation examples will further illustrate the present invention.

| Example 1 | |
|---|---|
| Paclitaxol | 10 g |
| Pluronic F108 | 5.0 g |
| Benzoate Sodium | 0.2 g |
| Saccharin Sodium | 0.1 g |
| FD & C Red No. 40 | 0.03 g |
| Water, qs | 100 ml |

-continued

Example 2

| | |
|---|---|
| Naproxen | 5.0 g |
| Pluronic F68 | 3.0 g |
| Benzoate Sodium | 0.2 g |
| Sorbate Potassium | 0.15 g |
| Saccharin Sodium | 0.1 g |
| FD & C Red No. 40 | 0.03 g |
| Water, qs | 100 ml |

Example 3

| | |
|---|---|
| Griseofulvin | 5.0 g |
| Pluronic F127 | 2.5 g |
| Benzoate Sodium | 0.2 g |
| Saccharin Sodium | 0.1 g |
| FD & C Red No. 3 | 0.03 g |
| Water, qs | 100 ml |

Example 4

| | |
|---|---|
| Paclitaxol | 0.5 g |
| Sucrose | 10 g |
| Pluronic F87 | .25 g |
| Dioctylsulfosuccinate | 0.1 g |
| Methylparabens | 0.2 g |
| Propylparabens | 0.07 g |
| FD & C Yellow No. 5 | 0.03 g |
| Water, qs | 100 ml |

Example 5

| | |
|---|---|
| Phenytoin | 5.0 g |
| Pluronic F108 | 2.5 g |
| Sorbitol | 5 g |
| Benzoate Sodium | 0.2 g |
| Water, qs | 100 ml |

The following Table 2 is a listing of formulations comprised of particles of therapeutic agents produced by wet grinding in the presence of the poloxamer listed which resulted in the particles having the poloxamer absorbed on the surface thereof. The weight average particle size of the resulting particles is also provided

TABLE 2

| Therapeutic Agent | Therapeutic Agent % | Poloxamer | % Poloxamer | Particle Size Weight Average |
|---|---|---|---|---|
| naproxen | 5% | F-68 | 3.0% | 270 nm |
| indomethacin | 5% | F-68 | 1% | 228 nm |
| indomethacin | 5% | F-68 | 2.5% | 193 nm |
| ibuprofen | 3% | F-68 | 2.0% | 253 nm |
| phenytoin | 5% | F-68 | 2.5% | 385 nm |
| phenytoin | 5% | F-108 | 2.5% | 385 nm |
| phenytoin | 5% | F-127 | 2.5% | 431 nm |
| griseofulvin | 5% | F-68 | 2.5% | 617 nm |
| griseofulvin | 5% | F-127 | 2.5% | 617 nm |
| amphotericin B | 5% | F-68 | 2.5% | 426 nm |
| amphotericin B | 5% | F-127 | 2.5% | 510 nm |
| methotrexate | 5% | F-68 | 2.5% | 196 nm |
| methotrexate | 5% | F-127 | 2.5% | 248 nm |
| beclomethasone dipropionate | 5% | F-68 | 2.5% | 221 nm |
| beclomethasone dipropionate | 5% | F-127 | 2.5% | 244 nm |
| cyclosporine | 5% | F-127 | 4.75% | 262 nm |
| cyclosporine | 5% | F-127 | 2.5% | 245 nm |
| cyclosporine | 5% | F-127 | 1.0% | 240 nm |
| cyclosporine | 5% | F-127 | 0.5% | 242 nm |
| camptothecin | 2% | F-68 | 2% | 107 nm |
| camptothecin | 2% | F-108 | 1% | 111 nm |
| busulfan | 2% | F-108 | 0.5% | 387 nm |
| piposulfan | 2% | F-108 | 0.5% | 339 nm |
| paclitaxol | 0.5% | F-68 | 0.13% | 172 nm |
| paclitaxol | 0.5% | F-68 | 0.25% | 247 nm |

TABLE 2-continued

| Therapeutic Agent | Therapeutic Agent % | Poloxamer | % Poloxamer | Particle Size Weight Average |
|---|---|---|---|---|
| paclitaxol | 0.5% | F-87 | 0.25% | 225 nm |
| paclitaxol | 0.5% | F-108 | 0.2% | 195 nm |
| paclitaxol | 0.5% | F-108 | 0.13% | 165 nm |
| paclitaxol | 0.5% | F-108 | 0.5% | 190 nm |
| paclitaxol | 0.5% | F-108 | 0.4% | 190 nm |
| paclitaxol | 0.5% | F-108 | 0.25% | 206 nm |
| paclitaxol | 0.5% | F-108 | 0.3% | 189 nm |
| paclitaxol | 1% | F-108 | 0.5% | 143 nm |
| paclitaxol | 2% | F-108 | 1% | 137 nm |
| paclitaxol | 5% | F-108 | 5% | 197 nm |
| paclitaxol | 5% | F-108 | 1.25% | 142 nm |
| paclitaxol | 5% | F-108 | 2.5% | 173 nm |
| paclitaxol | 2.3% | F-108 | 1.15% | 275 nm |
| paclitaxol | 6% | F-108 | 3% | 175 nm |
| paclitaxol | 10% | F-108 | 5% | 169 nm |

Determining Mucoadhesion Efficacy in the GI Tract

The amount and site of the mucoadhesion was determined by x-ray diagnostic imaging. The imaging was performed in anesthetized rats with the exception of G05-R1 samples which were imaged in fasted and anesthetized ferrets. Images were obtained using the Siemens C-Arm Siremobil 3U x-ray unit. The imaging dose was 10 ml/kg administered via gastric intubation to the anesthetized animal. X-rays were taken at 15, 30, 45 and 60 minutes and at 1, 2, 5 and 24 hours post-dose. A 10–15 ml volume of air was introduced to the animal at 30 minutes to produce a double contrast image.

Images were evaluated by the criteria of: coating, homogeneity, rate of gastric emptying and the total transit time. These are considered to be a measure of the stability of the suspension during transit down the GI tract and the ability of the formulation to adhere to the lower gastrointestinal tract. Suspensions were rated excellent when there was a uniform coating with transradiation of long intestinal segments, sufficient radiodensity to delineate anatomical structure, rapid emptying and transit, and stability and homogeneity during GI transit. A plus sign (+) was assigned when imaging in the lower GI was exceptional, a minus sign (−) as given when it was not. The suspension of the imaging agent [WIN 8883, ethyl 3,5-bis(acetylamino)-2,4,6-triodobenzoate], milled in Pluronic F127, was considered to be excellent for both upper and lower GI imaging in both rats and ferrets. All other suspensions were compared with this formulation.

The efficacy of the particulate formulations to image the GI tract is shown in Table 3.

TABLE 3

Imaging Efficacy of Particulate Formulations Prepared with Pluronic F127

| Code | WIN No. | Aqueous Solubility (μg/ml) | Days Milled | Milling Process[a] | Particle Size (nm)[b] | Range[c] | Imaging Efficacy [d,e] |
|---|---|---|---|---|---|---|---|
| GO5 | 8883 | <5 | 1.8 | P | 186/ND | Narrow | ++++(*) |
| GO5 R2 | 8883 | <5 | 5 | JM | 135/ND | 80–230 | ++++(*) |

[a]P = Planetary Mill, JM = Jar Mill
[b]Post-milling/pre-dose particle size; ND = Not Determined.
[c]Range(nm) = Size Distribution for 10 to 99% of the particles by weight.
[d]Imaging efficacy is indicated as follows:
Excellent ++++
Good +++
Fair ++
Poor +
[e]Formulations with efficacy followed by (*) signs indicate exceptional lower GI imaging while those with (−) sign were found to be unacceptable in the lower GI.

Efficacy of Particle Formulations Prepared with Alternate Stabilizers

The imaging efficacy of suspension formulations with alternate stabilizers are shown in Table 4. DOSS is Diioctylsulfosuccinate and was used as a secondary stabilizer is some formulations.

Excellent imaging was obtained from suspensions of WIN 8883 stabilized with Pluronic F77 with 0.1% DOSS added (G29) and with Pluronic F88 (GO4), however, these suspensions did not image the lower GI as effectively as GO5.

Good imaging was obtained from suspensions of WIN 8883 stabilized with F88 with 0.1% DOSS (G27), and F87 (G26). Good upper GI imaging was obtained from suspensions of WIN 8883 stabilized with F98 (G14), F108 (G15) and F68 with 0.1% w/v DOSS (G23). Fair imaging was obtained from the WIN 8883 suspensions stabilized F87 with 1% w/v DOSS (G25). Poor imaging was obtained when no stabilizer was used (GO2) and the formulation with F77 alone (G28) gelled during milling and therefore was not imaged.

DOSS was needed to stabilize the suspension prepared in 4% w/v Pluronic F77 (G29). The same formulation without DOSS could not be imaged due to gelling during the milling process.

DOSS had variable effects when used in conjunction with other stabilizers. The suspension stabilized with F88 (GO4) was rated as excellent. When 0.1% w/v DOSS was used as a secondary stabilizer (G24), the imaging efficacy was rated only as good. A similar result was noted with suspensions stabilized with F87. The suspension without DOSS (G26) was rated higher in imaging efficacy than did the same suspension with 0.1% w/v DOSS (G25). Suspensions stabilized with 4% w/v tyloxapol plus 0.1% w/v DOSS (G27) or without DOSS (G20) were both rated good. Milling time, however, was reduced and overall particle size was smaller with the DOSS-added suspension.

TABLE 4

Imaging Efficacy of Diagnostic Agents Prepared with Poloxamer and Alternative Stabilizers

| I.D. | Stabilizer (w/v) | Days Milled | Milling Process | Particle Size (nm)[b] | Range[c] | Imaging Efficacy [d,e,f] |
|---|---|---|---|---|---|---|
| GO2 | None | 6 | JM | 1000/ND | Broad | + |
| GO5 | 4% F127 | 1.8 | P | 186/ND | Narrow | ++++(*) |
| G29 | 4% F77/0.1% DOSS | 5 | JM | 146/187 | 66–243 | ++++ |
| EGO4 | 4% F88 | 1.8 | P | 183/ND | Narrow | ++++(−) |
| G21 | 4% PVA | 6 | JM | 204/199 | 134–405 | +++(*) |
| G26 | 4% F87 | 5 | JM | 155 | 55–265 | +++ |
| G20 | 4% Tyloxapol | 6 | JM | 180/262 | 137–521 | +++ |
| G22[f] | 2% HPMC | 6 | JM | 334/700 | 350–2596 | +++ |
| G24 | 4% F88/0.1% DOSS | 5 | JM | 160 | 146–265 | +++ |
| G27 | 4% Tyloxapol/ 0.1% DOSS | 5 | JM | 140 | 66–315 | +++ |
| G23 | 5% F68/0.1% DOSS | 4 | JM | 147/170 | 108–602 | +++(−) |
| GO3 | 4% Tween 80 | 6 | JM | 161/ND | Narrow | ++ |
| G18[f] | 1% DOSS | 4 | JM | 119/130 | 85–247 | ++ |
| G19[f] | 4% PVP | 5 | JM | 673/823 | 620–1265 | ++ |

TABLE 4-continued

Imaging Efficacy of Diagnostic Agents Prepared with
Poloxamer and Alternative Stabilizers

| I.D. | Stabilizer (w/v) | Days Milled | Milling Process | Particle Size (nm)[b] | Range[c] | Imaging Efficacy [d,e,f] |
|---|---|---|---|---|---|---|
| G25 | 4% F87/0.1% DOSS | 5 | JM | 150 | 66–243 | ++ |

[a]P = Planetary Mill, JM = Jar Mill, P(N)R = 18 hour planetary mill and N = number of days Jar Mill
[b]Post-milling/pre-dose particle size; ND = Not Determined. Formulations G24 through G28, G30 and G32 were sized within 24 hours of milling; others were sized when the milling was terminated.
[c]Range(nm) = Size Distribution for 10 to 99% of the particles by weight.
[d]Imaging efficacy is indicated as follows:
Excellent ++++
Good +++
Fair ++
P +
[e]Formulations with efficacy followed by (*) signs indicate exceptional lower GI imaging while those with (−) signs were found to be unacceptable in the lower GI.
[f]Foaming was evident in G18 (1% DOSS), very thick foam was found in G19 (4% PVP) and in G22 (2% HPMC).

TABLE 5

Comparison of Efficacy Between Pluronic F88 and Pluronic F127

| I.D. | WIN No | Pluronic | Days Milled | Milling Process [a] | Particle Size (nm)[b] | Range[c] | Imaging Efficacy [d,e] |
|---|---|---|---|---|---|---|---|
| GO5 | 8883 | F127 | 1.8 | P | 186/ND | Narrow | ++++(*) |
| GO4 | 8883 | F88 | 1.8 | P | 183/ND | Narrow | ++++(−) |

[a]P = Planetary Mill, JM = Jar Mill, P(N)R = 18 hour planetary mill and N = number of days Jar Mill
[b]Post-milling/pre-dose particle size; ND = Not Determined.
[c]Range(nm) = Size Distribution for 10 to 99% of the particles by weight (pre-image where indicated)
[d]Imaging efficacy is indicated as follows:
Excellent ++++
Good +++
Fair ++
P +
[e]Formulations with efficacy followed by (+) signs indicate exceptional lower GI imaging while those with (−) signs were found to be unacceptable in the lower GI.

Summarizing the above-described test results, many different stabilizers were examined using suspensions of WIN 8883, of these, Pluronic F127 was considered excellent for imaging both the upper and lower GI. A suspension stabilized with F88 was judged as excellent but for the upper GI only.

These studies indicate the site at which certain mucoadhesive stabilizers accrete, thus the formulator can use these studies to determine which stabilizer to utilize with a particular therapeutic agent in order to have the particles accrete at the desired site.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for targeting delivery of a pharmaceutical composition to the mucosal surface of the lower gastrointestinal tract (GIT) of a mammal comprising administering to a mammal a pharmaceutical composition comprising:
   (a) from about 0.1 to about 45% w/v of particles of an poorly water soluble crystalline therapeutic or diagnostic agent having an average particle size of less than about 2000 nm;
   (b) from about 0.1 to about 10% w/v of a polymer, wherein (i) the polymer is adsorbed on the surface of the therapeutic agent, and (ii) the polymer is selected from the group consisting of polyvinyl alcohol and poloxamer 407; and
   (c) water to make 100% w/v,
wherein the administration results in the drug being predominantly delivered to the lower GIT of the mammal.

2. The method according to claim 1, wherein the polymer is present in an amount of about 0.25 to about 5% w/v.

3. The method according to claim 1, wherein the average particle size of the agent is less than about 1000 nm.

4. The method according to claim 1, wherein the average particle size of the agent is less than about 400 nm.

5. The method according to claim 1, wherein the average particle size of the agent is less than about 300 nm.

6. The method according to claim 1, wherein the average particle size of the agent is less than about 200 nm.

7. The particles of claim 1, wherein the therapeutic or diagnostic agent is selected from the group consisting of analgesics, anti-inflammatory agents, anthelmintics, anti-arrhythmic agents, antibiotics, anticoagulants, antidepressants, antidiabetic agents, antiepileptics, antifungal agents, antihistamines, antihypertensive agents, antimuscarinic agents, antimycobacterial agents, antineoplastic agents, immunosuppressants, antithyroid agents, antiviral agents, anxiolytic sedatives, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, biphosphonates, protease inhibitors, prostaglandins, radiopharmaceuticals, sex hormones, steroids, anti-allergic agents, stimulants, sympathomimetics, thyroid agents, vasodilators and xanthines.

8. The method of claim 1, further comprising up to about 1% w/v of a secondary surface modifier.

9. The method of claim 8, wherein the secondary surface modifier is selected from the group consisting of dioctylsulfosuccinate and sodium lauryl sulfate.

10. A method for targeting delivery of a pharmaceutical composition to the mucosal surface of the upper gastrointestinal tract (GIT) of a mammal comprising administering to a mammal a pharmaceutical composition comprising:

(a) from about 0.1 to about 45% w/v of particles of a poorly water soluble crystalline therapeutic or diagnostic agent having an average particle size of less than about 2000 nm;

(b) from about 0.1 to about 10% w/v of a polymer, wherein (i) the polymer is adsorbed on the surface of the therapeutic agent, and (ii) the polymer is selected from the group consisting of poloxamer 238, a combination of poloxamer 188 and dioctyl sodium sulfosuccinate, poloxamer 288, and poloxamer 338; and (c) water to make 100% w/v, wherein the administration results in the drug being predominantly delivered to the upper GIT of the mammal.

11. The method of claim 10, wherein the secondary surface modifier is present in an amount of about 0.25 to about 5 w/v.

12. The method according to claim 10, wherein the average particle size of the agent is less than about 1000 nm.

13. The method according to claim 10, wherein the average particle size of the agent is less than about 400 nm.

14. The method according to claim 10, wherein the average particle size of the agent is less than about 300 nm.

15. The method according to claim 10, wherein the average particle size of the agent is less than about 200 nm.

16. The particles of claim 10, wherein the therapeutic or diagnostic agent is selected from the group consisting of analgesics, anti-inflammatory agents, anthelmintics, anti-arrhythmic agents, antibiotics, anticoagulants, antidepressants, antidiabetic agents, antiepileptics, antifungal agents, antihistamines, antihypertensive agents, antimuscarinic agents, antimycobacterial agents, antineoplastic agents, immunosuppressants, antithyroid agents, antiviral agents, anxiolytic sedatives, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, biphosphonates, protease inhibitors, prostaglandins, radiopharmaceuticals, sex hormones, steroids, anti-allergic agents, stimulants, sympathomimetics, thyroid agents, vasodilators and xanthines.

17. The method of claim 10, further comprising up to about 1% w/v of a secondary surface modifier.

18. The method of claim 17, wherein the secondary surface modifier is selected from the group consisting of dioctylsulfosuccinate and sodium lauryl sulfate.

19. A method for delivering a pharmaceutical composition homogeneously to the mucosal surface of both the upper and lower gastrointestinal tract (GIT) of a mammal comprising administering to a mammal a pharmaceutical composition comprising:

(a) from about 0.1 to about 45% w/v particles of a poorly water soluble crystalline therapeutic or diagnostic agent having an average particle size of less than about 2000 nm;

(b) from about 0.1 to about 10% w/v of a polymer, wherein (i) the polymer is adsorbed on the surface of the therapeutic agent, and (ii) the polymer is selected from the group consisting of:

(i) a mixture of poloxamer 217 and dioctyl sodium sulfosuccinate,
(ii) poloxamer 237;
(iii) a mixture of poloxamer 238 and dioctyl sodium sulfosuccinate;
(iv) a mixture of poloxamer 237 and dioctyl sodium sulfosuccinate;
(v) tyloxapol;
(vi) a mixture of tyloxapol and dioctyl sodium sulfosuccinate,
(vii) hydroxypropylmethyl cellulose,
(viii) polyvinylpyrrolidone,
(ix) dioctyl sodium sulfosuccinate, and
(x) polyoxyethylene (20) sorbitan monooleate; and (c) water to make 100% w/v, wherein the administration results in the drug being homogeneously delivered to the lower end upper GIT of the mammal.

20. The method according to claim 19, wherein the polymer is present in an amount of about 0.25 to about 5% w/v.

21. The method according to claim 19, wherein the average particle size of the agent is less than about 1000 nm.

22. The method according to claim 19, wherein the average particle size of the agent is less than about 400 nm.

23. The method according to claim 19, wherein the average particle size of the agent is less than about 300 nm.

24. The method according to claim 19, wherein the average particle size of the agent is less than about 200 nm.

25. The particles of claim 19, wherein the therapeutic or diagnostic agent is selected from the group consisting of analgesics, anti-inflammatory agents, anthelmintics, anti-arrhythmic agents, antibiotics, anticoagulants, antidepressants, antidiabetic agents, antiepileptics, antifungal agents, antihistamines, antihypertensive agents, antimuscarinic agents, antimycobacterial agents, antineoplastic agents, immunosuppressants, antithyroid agents, antiviral agents, anxiolytic sedatives, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, biphosphonates, protease inhibitors, prostaglandins, radiopharmaceuticals, sex hormones, steroids, anti-allergic agents, stimulants, sympathomimetics, thyroid agents, vasodilators and xanthines.

26. The method of claim 19, further comprising up to about 1% w/v of a secondary surface modifier.

27. The method of claim 26, wherein the secondary surface modifier is selected from the group consisting of dioctylsulfosuccinate and sodium lauryl sulfate.

* * * * *